United States Patent
Kim et al.

(10) Patent No.: US 10,662,450 B2
(45) Date of Patent: May 26, 2020

(54) ASPARTOKINASE VARIANT AND METHOD FOR PRODUCING L-AMINO ACID USING THE SAME

(71) Applicant: CJ Cheiljedang Corporation, Seoul (KR)

(72) Inventors: Hyung Joon Kim, Seoul (KR); Hyo Jin Kim, Gyeonggi-do (KR); Hyun Won Bae, Gyeonggi-do (KR); Hyun Ah Kim, Gyeonggi-do (KR); Chang Il Seo, Incheon (KR); Ji Sun Lee, Incheon (KR); Jin Sook Chang, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 16/344,189

(22) PCT Filed: Jun. 29, 2018

(86) PCT No.: PCT/KR2018/007407
§ 371 (c)(1),
(2) Date: Apr. 23, 2019

(87) PCT Pub. No.: WO2019/004778
PCT Pub. Date: Jan. 3, 2019

(65) Prior Publication Data
US 2020/0131545 A1  Apr. 30, 2020

(30) Foreign Application Priority Data

Jun. 30, 2017 (KR) .................. 10-2017-0083437

(51) Int. Cl.
*C12P 13/02* (2006.01)
*C12N 15/77* (2006.01)
*C12N 9/12* (2006.01)

(52) U.S. Cl.
CPC ............ *C12P 13/02* (2013.01); *C12N 9/1217* (2013.01); *C12N 15/77* (2013.01); *C12Y 207/02003* (2013.01)

(58) Field of Classification Search
None
See application file for complete search history.

(56) References Cited

U.S. PATENT DOCUMENTS

| 5,688,671 A | 11/1997 | Sugimoto et al. |
| 8,062,869 B2 | 11/2011 | Nakanishi et al. |
| 9,169,502 B2 | 10/2015 | Wittmann et al. |
| 2009/0253186 A1 | 10/2009 | Kim et al. |

FOREIGN PATENT DOCUMENTS

| JP | 3473042 B | 12/2003 |
| JP | 2007-068437 A | 3/2007 |
| KR | 10-2002-0065932 A | 4/2007 |
| KR | 10-0838038 B | 6/2008 |
| WO | WO 2003/040373 A2 | 5/2003 |

OTHER PUBLICATIONS

NCBI Protein Database, apartate kinase [Corynebacterium halotolerans YIM 70093 = DSM 44683] GenBank: AGF71327.1, Jun. 30, 2014.
Notice of Allowance issued in Korean Patent Application No. 9-5-2019-046165918, dated Jun. 27, 2019.
Office Action issued in Taiwanese Patent Application No. 10820656960, dated Jul. 10, 2019.
Ohnishi, J., et al. A novel methodology employing Corynebacterium glutamicum genome information to generate a new L-lysine-producing mutant. Applied microbiology and biotechnology, 2002, 58.2: 217-223.
NCBI, GenPept accession No. WP_015399751.1, May 19, 2013.

*Primary Examiner* — Suzanne M Noakes
*Assistant Examiner* — Jae W Lee
(74) *Attorney, Agent, or Firm* — Knobbe Martens Olson & Bear LLP

(57) ABSTRACT

An aspartokinase variant, a microorganism comprising the variant, and a method for producing an aspartate-derived L-amino acid or a homoserine derivative thereof using the microorganism.

8 Claims, 1 Drawing Sheet
Specification includes a Sequence Listing.

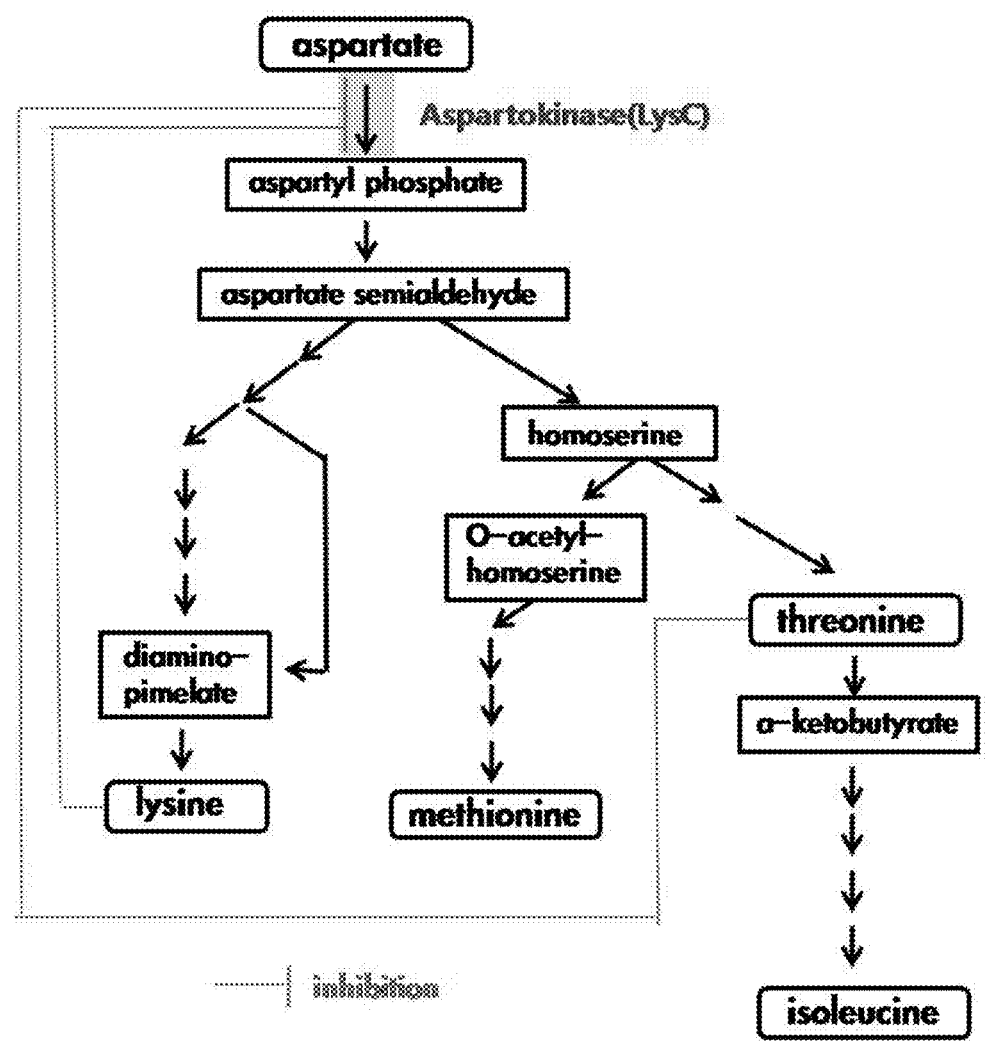

SEQUENCE LISTING

```
<160> NUMBER OF SEQ ID NOS: 36

<210> SEQ ID NO 1
<211> LENGTH: 421
<212> TYPE: PRT
<213> ORGANISM: Corynebacterium glutamicum

<400> SEQUENCE: 1

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
```

```
            50                  55                  60
Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
            290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 2
<211> LENGTH: 1266
<212> TYPE: DNA
<213> ORGANISM: Corynebacterium glutamicum

<400> SEQUENCE: 2
```

```
gtggccctgg tcgtacagaa atatggcggt tcctcgcttg agagtgcgga acgcattaga    60
aacgtcgctg aacggatcgt tgccaccaag aaggctggaa atgatgtcgt ggttgtctgc   120
tccgcaatgg gagacaccac ggatgaactt ctagaacttg cagcggcagt gaatcccgtt   180
ccgccagctc gtgaaatgga tatgctcctg actgctggtg agcgtatttc taacgctctc   240
gtcgccatgg ctattgagtc ccttggcgca gaagcccaat ctttcacggg ctctcaggct   300
ggtgtgctca ccaccgagcg ccacggaaac gcacgcattg ttgatgtcac tccaggtcgt   360
gtgcgtgaag cactcgatga gggcaagatc tgcattgttg ctggtttcca gggtgttaat   420
aaagaaaccc gcgatgtcac cacgttgggt cgtggtggtt ctgacaccac tgcagttgcg   480
ttggcagctg ctttgaacgc tgatgtgtgt gagatttact cggacgttga cggtgtgtat   540
accgctgacc cgcgcatcgt tcctaatgca cagaagctgg aaaagctcag cttcgaagaa   600
atgctggaac ttgctgctgt tggctccaag attttggtgc tgcgcagtgt tgaatacgct   660
cgtgcattca atgtgccact tcgcgtacgc tcgtcttata gtaatgatcc cggcactttg   720
attgccggct ctatggagga tattcctgtg aagaagcag tccttaccgg tgtcgcaacc   780
gacaagtccg aagccaaagt aaccgttctg ggtatttccg ataagccagg cgaggctgcg   840
aaggttttcc gtgcgttggc tgatgcagaa atcaacattg acatggttct gcagaacgtc   900
tcttctgtag aagacggcac caccgacatc accttcacct gccctcgttc cgacggccgc   960
cgcgcgatgg agatcttgaa gaagcttcag gttcagggca actggaccaa tgtgctttac  1020
gacgaccagg tcggcaaagt ctccctcgtg ggtgctggca tgaagtctca cccaggtgtt  1080
accgcagagt tcatggaagc tctgcgcgat gtcaacgtga acatcgaatt gatttccacc  1140
tctgagattc gtatttccgt gctgatccgt gaagatgatc tggatgctgc tgcacgtgca  1200
ttgcatgagc agttccagct gggcggcgaa gacgaagccg tcgtttatgc aggcaccgga  1260
cgctaa                                                             1266
```

<210> SEQ ID NO 3
<211> LENGTH: 421
<212> TYPE: PRT
<213> ORGANISM: Corynebacterium glutamicum

<400> SEQUENCE: 3

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140
```

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
            165                 170                 175

Asp Gly Val Tyr Thr Ala Asp Pro Arg Ile Val Pro Asn Ala Gln Lys
        180                 185                 190

Leu Glu Lys Leu Ser Phe Glu Glu Met Leu Glu Leu Ala Ala Val Gly
    195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Lys Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 4
<211> LENGTH: 1266
<212> TYPE: DNA
<213> ORGANISM: Corynebacterium glutamicum

<400> SEQUENCE: 4
gtggccctgg tcgtacagaa atatggcggt tcctcgcttg agagtgcgga acgcattaga    60
aacgtcgctg aacggatcgt tgccaccaag aaggctggaa atgatgtcgt ggttgtctgc   120
tccgcaatgg gagacaccac ggatgaactt ctagaacttg cagcggcagt gaatcccgtt   180
ccgccagctc gtgaaatgga tatgctcctg actgctggtg agcgtatttc taacgctctc   240
gtcgccatgg ctattgagtc ccttggcgca gaagcccaat cttttcacgg gctctcaggct   300 ggtgtgctca ccaccgagcg ccacggaaac gcacgcattg ttgatgtcac tccaggtcgt   360
gtgcgtgaag cactcgatga gggcaagatc tgcattgttg ctggttttcca gggtgttaat   420 aaagaacccc gcgatgtcac cacgtttggg cgtggtggtt ctgacaccac tgcagttgcg   480
ttggcagctg ctttgaacgc tgatgtgtgt gagatttact cggacgttga cggtgtgtat   540

```
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcactttg    720
attgccggct ctatggagga tattcctgtg aagaagcag tccttaccgg tgtcgcaacc     780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc accttcacct gccctcgttc cgacggccgc    960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaaaa gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa    1266
```

<210> SEQ ID NO 5
<211> LENGTH: 421
<212> TYPE: PRT
<213> ORGANISM: Corynebacterium glutamicum

<400> SEQUENCE: 5

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240
```

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Met Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 6
<211> LENGTH: 1266
<212> TYPE: DNA
<213> ORGANISM: Corynebacterium glutamicum

<400> SEQUENCE: 6

| | |
|---|---|
| gtggccctgg tcgtacagaa atatggcggt tcctcgcttg agagtgcgga acgcattaga | 60 |
| aacgtcgctg aacggatcgt tgccaccaag aaggctggaa atgatgtcgt ggttgtctgc | 120 |
| tccgcaatgg gagacaccac ggatgaactt ctagaacttg cagcggcagt gaatcccgtt | 180 |
| ccgccagctc gtgaaatgga tatgctcctg actgctggtg agcgtatttc taacgctctc | 240 |
| gtcgccatgg ctattgagtc ccttggcgca gaagcccaat cttttcacggg ctctcaggct | 300 |
| ggtgtgctca ccaccgagcg ccacggaaac gcacgcattg ttgatgtcac tccaggtcgt | 360 |
| gtgcgtgaag cactcgatga gggcaagatc tgcattgttg ctggtttcca gggtgttaat | 420 |
| aaagaaaccc gcgatgtcac cacgttgggt cgtggtggtt ctgacaccac tgcagttgcg | 480 |
| ttggcagctg ctttgaacgc tgatgtgtgt gagatttact cggacgttga cggtgtgtat | 540 |
| accgctgacc cgcgcatcgt tcctaatgca cagaagctgg aaaagctcag cttcgaagaa | 600 |
| atgctggaac ttgctgctgt tggctccaag attttggtgc tgcgcagtgt tgaatacgct | 660 |
| cgtgcattca atgtgccact tcgcgtacgc tcgtcttata gtaatgatcc cggcactttg | 720 |
| attgccggct ctatggagga tattcctgtg gaagaagcag tccttaccgg tgtcgcaacc | 780 |
| gacaagtccg aagccaaagt aaccgttctg ggtatttccg ataagccagg cgaggctgcg | 840 |
| aaggttttcc gtgcgttggc tgatgcagaa atcaacattg acatggttct gcagaacgtc | 900 |
| tcttctgtag aagacggcac caccgacatc accttcacct gccctcgttc cgacggccgc | 960 |
| cgcgcgatgg agatcttgaa gaagcttcag gttcagggca actggaccaa tgtgctttac | 1020 |

```
gacgaccagg tcggcaaagt ctccctcgtg ggtgctggca tgaagtctca cccaggtgtt    1080
accgcagagt tcatggaagc tctgcgcgat gtcaacgtga acatcgaaat gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266

<210> SEQ ID NO 7
<211> LENGTH: 29
<212> TYPE: DNA
<213> ORGANISM: Artificial Sequence
<220> FEATURE:
<223> OTHER INFORMATION: primer 1

<400> SEQUENCE: 7
tcctctagag ctgcgcagtg ttgaatacg                                      29

<210> SEQ ID NO 8
<211> LENGTH: 30
<212> TYPE: DNA
<213> ORGANISM: Artificial Sequence
<220> FEATURE:
<223> OTHER INFORMATION: primer 2

<400> SEQUENCE: 8
tggaaatctt ttcgatgttc acgttgacat                                     30

<210> SEQ ID NO 9
<211> LENGTH: 30
<212> TYPE: DNA
<213> ORGANISM: Artificial Sequence
<220> FEATURE:
<223> OTHER INFORMATION: primer 3

<400> SEQUENCE: 9
acatcgaaaa gatttccacc tctgagattc                                     30

<210> SEQ ID NO 10
<211> LENGTH: 30
<212> TYPE: DNA
<213> ORGANISM: Artificial Sequence
<220> FEATURE:
<223> OTHER INFORMATION: primer 4

<400> SEQUENCE: 10
tggaaatcat ttcgatgttc acgttgacat                                     30

<210> SEQ ID NO 11
<211> LENGTH: 30
<212> TYPE: DNA
<213> ORGANISM: Artificial Sequence
<220> FEATURE:
<223> OTHER INFORMATION: primer 5

<400> SEQUENCE: 11
acatcgaaat gatttccacc tctgagattc                                     30

<210> SEQ ID NO 12
<211> LENGTH: 29
<212> TYPE: DNA
<213> ORGANISM: Artificial Sequence
<220> FEATURE:
<223> OTHER INFORMATION: primer 6

<400> SEQUENCE: 12
```

-continued

```
gactctagag ttcacctcag agacgatta                                29
```

<210> SEQ ID NO 13
<211> LENGTH: 29
<212> TYPE: DNA
<213> ORGANISM: Artificial Sequence
<220> FEATURE:
<223> OTHER INFORMATION: primer 7

<400> SEQUENCE: 13

```
tcctctagac tggtcgcctg atgttctac                                29
```

<210> SEQ ID NO 14
<211> LENGTH: 20
<212> TYPE: DNA
<213> ORGANISM: Artificial Sequence
<220> FEATURE:
<223> OTHER INFORMATION: primer 8

<400> SEQUENCE: 14

```
gccaaaacct ccacgcgatc                                          20
```

<210> SEQ ID NO 15
<211> LENGTH: 20
<212> TYPE: DNA
<213> ORGANISM: Artificial Sequence
<220> FEATURE:
<223> OTHER INFORMATION: primer 9

<400> SEQUENCE: 15

```
atcgcgtgga ggttttggct                                          20
```

<210> SEQ ID NO 16
<211> LENGTH: 29
<212> TYPE: DNA
<213> ORGANISM: Artificial Sequence
<220> FEATURE:
<223> OTHER INFORMATION: primer 10

<400> SEQUENCE: 16

```
gactctagat tagtcccttt cgaggcgga                                29
```

<210> SEQ ID NO 17
<211> LENGTH: 28
<212> TYPE: DNA
<213> ORGANISM: Artificial Sequence
<220> FEATURE:
<223> OTHER INFORMATION: primer 11

<400> SEQUENCE: 17

```
acggatccca gactccaaag caaaagcg                                 28
```

<210> SEQ ID NO 18
<211> LENGTH: 30
<212> TYPE: DNA
<213> ORGANISM: Artificial Sequence
<220> FEATURE:
<223> OTHER INFORMATION: primer 12

<400> SEQUENCE: 18

```
acaccacggc agaaccaggt gcaaaggaca                               30
```

<210> SEQ ID NO 19
<211> LENGTH: 30
<212> TYPE: DNA

<213> ORGANISM: Artificial Sequence
<220> FEATURE:
<223> OTHER INFORMATION: primer 13

<400> SEQUENCE: 19
ctggttctgc cgtggtgtgc atcatctctg                                      30

<210> SEQ ID NO 20
<211> LENGTH: 28
<212> TYPE: DNA
<213> ORGANISM: Artificial Sequence
<220> FEATURE:
<223> OTHER INFORMATION: primer 14

<400> SEQUENCE: 20
acggatccaa ccaaacttgc tcacactc                                        28

<210> SEQ ID NO 21
<211> LENGTH: 24
<212> TYPE: DNA
<213> ORGANISM: Artificial Sequence
<220> FEATURE:
<223> OTHER INFORMATION: primer 15

<400> SEQUENCE: 21
tctagatgcg ctgattatct cacc                                            24

<210> SEQ ID NO 22
<211> LENGTH: 40
<212> TYPE: DNA
<213> ORGANISM: Artificial Sequence
<220> FEATURE:
<223> OTHER INFORMATION: primer 16

<400> SEQUENCE: 22
actggtgggt catggttgca tatgagatca actcctgtaa                           40

<210> SEQ ID NO 23
<211> LENGTH: 40
<212> TYPE: DNA
<213> ORGANISM: Artificial Sequence
<220> FEATURE:
<223> OTHER INFORMATION: primer 17

<400> SEQUENCE: 23
ttacaggagt tgatctcata tgcaaccatg acccaccagt                           40

<210> SEQ ID NO 24
<211> LENGTH: 24
<212> TYPE: DNA
<213> ORGANISM: Artificial Sequence
<220> FEATURE:
<223> OTHER INFORMATION: primer 18

<400> SEQUENCE: 24
tctagacctt gaagttcttg actg                                            24

<210> SEQ ID NO 25
<211> LENGTH: 24
<212> TYPE: DNA
<213> ORGANISM: Artificial Sequence
<220> FEATURE:
<223> OTHER INFORMATION: primer 19

<400> SEQUENCE: 25
tctagaagta gcgttgctgt acac                                            24

<210> SEQ ID NO 26
<211> LENGTH: 43
<212> TYPE: DNA
<213> ORGANISM: Artificial Sequence
<220> FEATURE:
<223> OTHER INFORMATION: primer 20

<400> SEQUENCE: 26
atcaatggtc tcgatgccca tatggcattt ggaggtcctt aag                43

<210> SEQ ID NO 27
<211> LENGTH: 43
<212> TYPE: DNA
<213> ORGANISM: Artificial Sequence
<220> FEATURE:
<223> OTHER INFORMATION: primer 21

<400> SEQUENCE: 27
cttaaggacc tccaaatgcc atatgggcat cgagaccatt gat                43

<210> SEQ ID NO 28
<211> LENGTH: 24
<212> TYPE: DNA
<213> ORGANISM: Artificial Sequence
<220> FEATURE:
<223> OTHER INFORMATION: primer 22

<400> SEQUENCE: 28
tctagatgga accgttgcaa ccac                                     24

<210> SEQ ID NO 29
<211> LENGTH: 28
<212> TYPE: DNA
<213> ORGANISM: Artificial Sequence
<220> FEATURE:
<223> OTHER INFORMATION: primer 23

<400> SEQUENCE: 29
ggatcccctc gttgttcacc cagcaacc                                 28

<210> SEQ ID NO 30
<211> LENGTH: 30
<212> TYPE: DNA
<213> ORGANISM: Artificial Sequence
<220> FEATURE:
<223> OTHER INFORMATION: primer 24

<400> SEQUENCE: 30
ggatcccaaa gtcacaacta cttatgttag                               30

<210> SEQ ID NO 31
<211> LENGTH: 26
<212> TYPE: DNA
<213> ORGANISM: Artificial Sequence
<220> FEATURE:
<223> OTHER INFORMATION: primer 25

<400> SEQUENCE: 31
tctagaatgc ccaccctcgc gccttc                                   26

<210> SEQ ID NO 32
<211> LENGTH: 25
<212> TYPE: DNA
<213> ORGANISM: Artificial Sequence
<220> FEATURE:

```
<223> OTHER INFORMATION: primer 26

<400> SEQUENCE: 32
tctagattag atgtagaact cgatg                                            25

<210> SEQ ID NO 33
<211> LENGTH: 35
<212> TYPE: DNA
<213> ORGANISM: Artificial Sequence
<220> FEATURE:
<223> OTHER INFORMATION: primer 27

<400> SEQUENCE: 33
acgcgccagc gcctggaaca tcggcattca atccg                                 35

<210> SEQ ID NO 34
<211> LENGTH: 35
<212> TYPE: DNA
<213> ORGANISM: Artificial Sequence
<220> FEATURE:
<223> OTHER INFORMATION: primer 28

<400> SEQUENCE: 34
cggattgaat gccgatgttc caggcgctgg cgcgt                                 35

<210> SEQ ID NO 35
<211> LENGTH: 33
<212> TYPE: DNA
<213> ORGANISM: Artificial Sequence
<220> FEATURE:
<223> OTHER INFORMATION: primer 29

<400> SEQUENCE: 35
gtagataccg atattcggta cccctaccac cag                                   33

<210> SEQ ID NO 36
<211> LENGTH: 33
<212> TYPE: DNA
<213> ORGANISM: Artificial Sequence
<220> FEATURE:
<223> OTHER INFORMATION: primer 30

<400> SEQUENCE: 36
ctggtggtag gggtaccgaa tatcggtatc tac                                   33
```

ASPARTOKINASE VARIANT AND METHOD FOR PRODUCING L-AMINO ACID USING THE SAME

CROSS-REFERENCE TO RELATED APPLICATIONS

This application is a U.S. National Phase Application of PCT International Application No. PCT/KR2018/007407, filed on Jun. 29, 2018, designating the United States of America, which is an International Application of and claims the benefit of priority to Korean Patent Application No. 10-2017-0083437, filed on Jun. 30, 2017, the entire contents of which are incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing_HAN030-008APC.txt," which was created on Apr. 23, 2019, and is approximately 22 kb in size. This Sequence Listing is hereby incorporated by reference.

TECHNICAL FIELD

The present disclosure relates to an aspartokinase variant, a microorganism comprising the variant, and a method for producing an aspartate-derived L-amino acid or an amino acid derivative thereof by using the microorganism.

BACKGROUND ART

A microorganism of the genus *Corynebacterium*, particularly *Corynebacterium glutamicum*, is a gram-positive microorganism which is widely used for the production of L-amino acids and other useful substances. In order to produce L-amino acids and other useful substances, various studies have been conducted to develop high-efficiency production microorganisms and technology for fermentation processes. For example, methods for specifically approaching target substances by increasing the expression of genes encoding enzymes involved in L-lysine biosynthesis or by knocking out genes unnecessary for biosynthesis have been mainly used (Korean Patent No. 10-0838038).

Meanwhile, among the L-amino acids, L-lysine, L-threonine, L-methionine, L-isoleucine, and L-glycine are amino acids derived from aspartate (Asp), and these amino acids commonly use aspartyl phosphate (App) produced from Asp by aspartokinase (LysC, E.C. 2.7.2.4) (FIG. 1). Therefore, in order to produce the amino acids by a microbial fermentation method, it is essential to maintain the activities of enzymes used in the biosynthetic pathway at a certain level or higher, and thus intensive research has been carried out in this regard.

In particular, the activity of LysC, which acts as the first enzyme in the biosynthesis pathway of aspartate-derived amino acids, is known to be regulated by feedback inhibition of L-lysine and L-threonine (J Mol Biol. 2007 Apr. 27; 368(2):521-36. Epub 2007 Feb. 20). In this regard, although applications relevant to the feedback inhibition have been filed (U.S. Pat. No. 8,062,869 B and Japanese Patent No. JP 3473042 B), continued research is still required for increasing the productivity of aspartate-derived products.

Under such circumstances, the present inventors have completed the present disclosure by confirming that production of aspartate-derived L-amino acids or amino acid derivatives thereof is improved when using a novel aspartokinase variant.

DISCLOSURE

Technical Problem

An objective of the present disclosure is to provide an aspartokinase variant comprising one or more amino acid substitution in the amino acid sequence of SEQ ID NO: 1, wherein the amino acid substitution comprises that the amino acid at position 377 in the amino acid sequence of SEQ ID NO: 1 is substituted with L-lysine or L-methionine.

Another objective of the present disclosure is to provide a polynucleotide encoding the variant.

Still another objective of the present disclosure is to provide a microorganism of the genus *Corynebacterium* producing an aspartate-derived L-amino acid or an amino acid derivative thereof, which comprises the aspartokinase variant or has the enhanced activity thereof.

Still another objective of the present disclosure is to provide a method for producing an aspartate-derived L-amino acid or an amino acid derivative thereof, comprising: culturing the microorganism in a medium; and recovering the aspartate-derived L-amino acid or amino acid derivative thereof from the cultured microorganism or cultured medium.

Still another objective of the present disclosure is to provide a method for producing methionine, comprising: culturing the microorganism in a medium; producing acetylhomoserine or succinylhomoserine from the cultured microorganism or cultured medium; and converting the acetylhomoserine or succinylhomoserine to methionine.

Technical Solution

Hereinbelow, the present disclosure will be described in detail.

Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

Additionally, one of ordinary skill in the art will be able to recognize or confirm, based on routine experimentation, many equivalents to the specific embodiments of the present disclosure described in this application, and such equivalents are intended to be included in the present disclosure.

In order to achieve the objectives above, an aspect of the present disclosure provides an aspartokinase variant comprising one or more amino acid substitution in the amino acid sequence of SEQ ID NO: 1, wherein the amino acid substitution comprises that the amino acid at position 377 is substituted with another amino acid. Specifically, an objective of the present disclosure is to provide an aspartokinase variant, wherein the amino acid at position 377 in the amino acid sequence of SEQ ID NO: 1 is substituted with L-lysine or L-methionine.

As used herein, the term "aspartokinase" refers to an enzyme that catalyzes the phosphorylation of an amino acid, aspartate, and acts in the first step of biosynthesizing three essential amino acids, L-methionine, L-lysine, and L-threonine, which are known as the aspartate family.

In the present disclosure, the term "aspartokinase" can interchangeably be used with "LysC" or "LysC protein". The LysC protein can be obtained from GenBank of NCBI, a known database. The LysC protein may be LysC derived from the genus *Corynebacterium*, and specifically, may be a polypeptide having an amino acid sequence of SEQ ID NO: 1, which is derived from *Corynebacterium glutamicum*, but is not limited thereto. In addition, the LysC in the present disclosure may be a polypeptide consisting of the amino acid sequence of SEQ ID NO: 1 or an amino acid sequence having a homology or identity thereto of 80%, 85%, 90%, 95%, or 97% or higher. Additionally, it is apparent that a polypeptide having an amino acid sequence with deletion, modification, substitution, or addition of a part of the sequence is also included within the scope of the present disclosure as long as the amino acid sequence has such a homology or identity and exhibits an effect corresponding to that of the polypeptide.

In the present disclosure, various methods well known in the art may be used for the method for obtaining aspartokinase (LysC). Examples of such methods include gene synthesis techniques including optimization of codons so as to obtain enzymes at high efficiency in a microorganism of the genus *Corynebacterium*, which is commonly used for the expression of enzymes, and methods for screening useful enzyme resources using bioinformatic methods based on meta-genome of microorganisms, but the methods are not limited thereto.

As used herein, the term "variant" is a polypeptide that at least one amino acid differs from the recited polypeptide in conservative substitutions and/or modifications, such that the functions or properties of the polypeptide are retained. Variant polypeptides differ from an identified sequence by substitution, deletion or addition of several amino acids. Such variants may generally be identified by modifying one of the above polypeptide sequences, and evaluating the properties of the modified polypeptide. In other words, the ability of a variant may be enhanced, unchanged, or diminished relative to the native protein. Such variants may generally be identified by modifying one of the above polypeptide sequences and evaluating the reactivity of the modified polypeptide. Further, a part of variants may include those in which one or more portions, such as an N-terminal leader sequence or transmembrane domain, have been removed. Other variants may include variants in which a small portion has been removed from the N- and/or C-terminal of the mature protein.

As used herein, a "conservative substitution" means that an amino acid is substituted for another amino acid that has similar structural and/or chemical properties. For example, the variants may have at least one conservative substitution with retaining one more biological activity. Such amino acid substitutions may generally be made on the basis of similarity in polarity, charge, solubility, hydrophobicity, hydrophilicity and/or the amphipathic nature of the residues. For example, positively charged (basic) amino acids include arginine, lysine and histidine; negatively charged (acidic) amino acids include aspartic acid and glutamic acid; aromatic amino acids include phenylalanine, tryptophan and tyrosine; and hydrophobic amino acids include alanine, valine, isoleucine, leucine, methionine, phenylalanine, tyrosine and tryptophan. Typically, conservative substitutions have little to no impact on the activity of a resulting polypeptide.

Variants may also contain other modifications, including the deletion or addition of amino acids that have minimal influence on the properties and secondary structure of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide.

For example, the term "Aspartokinase variant" claimed herein may specifically refer to a modified polypeptide of LysC having the amino acid sequence of SEQ ID NO: 1 which is derived from *Corynebacterium* sp., and may comprises a variant comprising one or more amino acid substitution in the amino acid sequence of SEQ ID NO: 1. Specifically it may a variant comprises that the amino acid residue at position 377 is substituted with another amino acid in the amino acid sequence of SEQ ID NO: 1. The "other amino acid" is not limited as long as it is an amino acid other than L-leucine, which is the amino acid at position 377. Specifically, for example, the amino acid residue at position 377 may be substituted with lysine or methionine. L-Lysine is an example of a basic amino acid, and the basic amino acid may be one of L-lysine, L-arginine, and L-histidine. L-Methionine is an example of a non-polar amino acid, and the non-polar amino acid may be one of L-methionine, L-phenylalanine, L-alanine, L-cysteine, L-glycine, L-isoleucine, L-leucine, L-proline, L-tryptophan, and L-valine. However, these are not limited thereto.

As used herein, the term "aspartokinase variant" may interchangeably be used with "modified aspartokinase" or "modified LysC".

Such aspartokinase variant is characterized by having an enhanced activity of aspartokinase compared to the polypeptide having an activity of aspartokinase of SEQ ID NO: 1.

Additionally, even if it is described herein as a "protein having an amino acid sequence of a specific sequence number", it is apparent that a polypeptide having an amino acid sequence with deletion, modification, substitution, or addition of a part of the sequence is also included within the scope of the present disclosure as long as the protein has the effect identical or equivalent to that of the peptide consisting of the amino acid sequence of the corresponding sequence number. Specifically, such protein does not exclude an addition of sequences which have no alter the function of on the protein at the front or the end of the amino acid sequence of the corresponding sequence number, a naturally occurring mutation, conservative substitution or a synonymous mutation thereof. In addition, it is apparent that the protein having such sequence addition or mutation is also included within the scope of the present disclosure.

As used herein, the term "conservative substitution" refers to substitution of a certain amino acid residue with an amino acid residue having a similar side chain. Families of amino acid residues having similar side chains are well-known in the art. Examples of such families may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a branched side chain at position (3 (e.g., threonine, valine, isoleucine), amino acids having an aromatic side chain (e.g., tyrosine, phenylalanine, tryptophan, histidine), amino acids having a hydroxyl group-containing (e.g., alcoholic, phenolic) side chain (e.g., serine, threonine, tyrosine), and amino acids having a sulfur-containing side chain (e.g., cysteine, methionine). Preferably, the conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

As used herein, the term "homology" or "identity" refers to the degree of relevance between two given amino acid sequences or nucleotide sequences and can be expressed as a percentage.

The terms "homology" and "identity" are often used interchangeably with each other. The sequence homology or identity of conserved polynucleotide or polypeptide sequences may be determined by standard alignment algorithms and can be used with default gap penalty established by the program being used. Substantially homologous or identical polynucleotides or polypeptides are generally expected to hybridize at least about 50%, about 60%, about 70%, about 80% or about 90% of the entire length of the target polynucleotides or polypeptides under moderate or high stringent condition. Polynucleotides that contain degenerate codons instead of codons are also considered for the hybridization.

Whether any two polynucleotide or polypeptide sequences have a homology, similarity or identity each other, it may be determined using a known computer algorithm such as the "FASTA" program (e.g., Pearson et al., (1988) *Proc. Natl. Acad. Sci. USA* 85: 2444) using default parameters. Alternatively, it may be determined using the Needleman-Wunsch algorithm (Needleman and Wunsch, 1970, *J. Mol. Biol.* 48: 443-453), which is performed in the Needleman program of the EMBOSS package (EMBOSS: The European Molecular Biology Open Software Suite, Rice et al., 2000, *Trends Genet.* 16: 276-277) (preferably, version 5.0.0 or versions thereafter) (GCG program package (Devereux, J., et al., *Nucleic Acids Research* 12: 387 (1984)), BLASTP, BLASTN, FASTA (Atschul, [S.] [F.,] [ET AL., *J MOLEC BIOL* 215]: 403 (1990); Guide to Huge Computers, Martin J. Bishop, [ED.,] Academic Press, San Diego, 1994, and [CARILLO ETA/.](1988) SIAM *J Applied Math* 48: 1073). For example, the homology or identity may be determined using BLAST or ClustalW of the National Center for Biotechnology Information (NCBI).

The homology, similarity or identity of polynucleotide or polypeptide sequences may be determined by comparing sequence information using, for example, the GAP computer program (e.g., Smith and Waterman, *Adv. Appl. Math* (1981) 2:482) as published. In summary, the GAP program defines the homology or identity as the value obtained by dividing the number of similarly aligned symbols (i.e. nucleotides or amino acids) by the total number of the symbols in the shorter of the two sequences. Default parameters for the GAP program may include (1) a unary comparison matrix (containing a of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to relevance between sequences.

Another aspect of the present disclosure provides a polynucleotide encoding the aspartokinase variant.

The aspartokinase variant is as described above.

As used herein, the term "polynucleotide" refers to a nucleotide polymer composed of nucleotide monomers covalently bonded in a chain, and examples thereof are DNA or RNA strands having a predetermined or longer length. Specifically, the polynucleotide refers to a polynucleotide fragment encoding the modified polypeptide.

The polynucleotide encoding the aspartokinase variant may be a polynucleotide encoding a polypeptide comprising one or more amino acid substitution in the amino acid sequence of SEQ ID NO: 1, in which the amino acid substitution comprises that the amino acid residue at position 377 is substituted with another amino acid. Specifically, as a representative example, the polynucleotide encoding the aspartokinase variant may be a polynucleotide encoding a polypeptide in which the amino acid residue at position 377 is substituted with another amino acid of L-lysine or L-methionine in the amino acid sequence of SEQ ID NO: 1. More specifically, the polynucleotide may be a polynucleotide encoding a LysC protein having the amino acid sequence consisting of SEQ ID NO: 3 or SEQ ID NO: 5. For example, the polynucleotide may be a polynucleotide consisting of the nucleotide sequence of SEQ ID NO: 4 or SEQ ID NO: 6. Various modifications may be made in the coding region provided that they do not change the amino acid sequence of the protein expressed from the coding region, due to codon degeneracy or in consideration of the codons preferred by an organism in which the protein is to be expressed.

Therefore, it is apparent that due to codon degeneracy, the polypeptide consisting of the amino acid sequence of SEQ ID NO: 3 or SEQ ID NO: 5 or the polynucleotide capable of being translated into a polynucleotide having homology or identity thereto can also be included in the scope of the present disclosure. Alternately, a probe that can be prepared from a known gene sequence, for example, a sequence encoding a protein having the activity of the enzyme consisting of the amino acid sequence of SEQ ID NO: 1 by hybridizing under stringent conditions with a complementary sequence to all or a part of the polynucleotide sequence, can be included without limitation.

The "stringent conditions" refer to the conditions which allow the specific hybridization between the polynucleotides. Such conditions are specifically disclosed in the literature (e.g., J. Sambrook et al.). For example, the stringent conditions may include a condition in which genes having a high homology or identity (e.g., 80% or more, 85% or more, specifically 90% or more, more specifically 95% or more, even more specifically 97% or more, and even more specifically 99% or more) can hybridize between them, whereas genes having a lower homology or identity thereof cannot hybridize with each other; or conditions for conventional southern hybridization (i.e., conditions for washing once, and specifically two or three times under a salt concentration and temperature corresponding to 60° C., 1 xSSC, and 0.1% SDS; specifically under 60° C., 0.1 xSSC, and 0.1% SDS; and more specifically under 68° C., 0.1× SSC, and 0.1% SDS).

Hybridization requires that two nucleic acids have complementary sequences, although mismatches between bases are possible depending on the severity of hybridization. The term "complementary" is used to describe the relationship between nucleotide bases that are capable of being hybridized with each other. For example, with respect to DNA, adenosine is complementary to thymine and cytosine is complementary to guanine. Therefore, the present disclosure may also include substantially similar nucleic acid sequences as well as isolated nucleic acid fragments complementary to the entire sequence.

Specifically, the polynucleotide having homology or identity can be detected using hybridization conditions including a hybridization step at a $T_m$ value of 55° C. and using the above-described conditions. In addition, the $T_m$ value may be 60° C., 63° C., or 65° C., but is not limited thereto. One of ordinary skill in the art can appropriately adjust the $T_m$ value according to its purpose.

The appropriate stringency of hybridizing the polynucleotides is dependent on the length and degree of complementarity of the polynucleotides, and the variables are well known in the art (Sambrook et al., supra, 9.50-9.51, 11.7-11.8).

Still another aspect of the present disclosure provides a host cell containing the aspartokinase variant and a microorganism transformed with a vector containing a polynucleotide encoding the aspartokinase variant. Specifically, the present disclosure provides a microorganism of the genus Corynebacterium producing an aspartate-derived L-amino acid or an amino acid derivative thereof, which comprises the aspartokinase variant.

The microorganism containing the aspartokinase variant of the present disclosure is characterized in that the activity of aspartokinase is enhanced compared to the wild-type or unmodified microorganism.

As used herein, the term "enhancement of activity" means that the activity of a protein is introduced, or that the activity is enhanced as compared with the intrinsic activity or the pre-modification activity of a microorganism. The "introduction" of the activity means that the activity of a specific protein that the microorganism did not originally have is naturally or artificially expressed. The "intrinsic activity" refers to the activity of a specific protein, which is originally present in a parent strain before transformation, when microbial traits are altered by genetic variation by natural or artificial factors.

As used herein, the term "vector" refers to the DNA construct comprising the nucleotide sequence of the polynucleotide encoding the target protein operably linked to the proper regulatory sequence to express the target protein in the proper host. The regulatory sequence can include the promoter which can initiate transcription, any operator sequence to control the transcription, the sequence to encode the appropriate mRNA ribosome binding site, and the sequence to control the termination of transcription and translation. The vector may be transfected into a suitable host, and then may be replicated or function independently from the host genome, and may be integrated into the genome itself.

The vector used in the present disclosure is not particularly limited as long as it can be expressed in the host, and any vector which in known in the art may be used. Examples of commonly used vectors are a plasmid, cosmid, virus, and bacteriophage in a natural state or recombinant state. For example, pWE15, M13, MBL3, MBL4, IXII, ASHII, APII, t10, t11, Charon4A, and Charon21A can be used as a phage vector or cosmid vector; and pBR system, pUC system, pBluescriptII system, pGEM system, pTZ system, pCL system, and pET system can be used as a plasmid vector. Specifically, pDZ, pACYC177, pACYC184, pCL, pECCG117, pUC19, pBR322, pMW118, and pCC1BAC vectors can be used, but these are not limited thereto.

The vector that can be used in the present disclosure is not particularly limited, and a known expression vector can be used. In addition, a polynucleotide encoding a target protein can be inserted into a chromosome through a vector for intracellular chromosome insertion. The insertion of the polynucleotide into the chromosome may be performed by any method known in the art such as homologous recombination, without being particularly limited thereto. The vector may further include a selection marker for indicating the insertion of the vector into the host chromosome. The selection marker is used to select the cells transformed with the vector, that is, to confirm whether a target nucleic acid molecule is inserted. Therefore, the selection marker may endow the cell with an ability to show drug resistance, cytotoxic agent resistance, autotrophy, or selectable phenotype expression such as the expression of a surface protein. In the presence of a selective agent, transformed cells may be selected because only the cells which express the selection marker rendering survive or show another phenotype.

As used herein, the term "transformation" refers to the introduction of a vector including a polynucleotide encoding a target protein into a host cell in such a way that the protein encoded by the polynucleotide is expressed in the host cell. As long as the transformed polynucleotide can be expressed in the host cell, it can be either integrated into or placed in the chromosome of the host cell, or exist extrachromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may include a promoter operably linked to the polynucleotide, transcription terminator, ribosome binding sites, or translation terminator. The expression cassette may be in the form of a self-replicable expression vector. In addition, the polynucleotide as it is may be introduced into the host cell and operably linked to sequences required for expression in the host cell, but is not limited thereto. The transformation method includes any method of introducing a nucleic acid into a cell, and may be carried out by selecting a suitable standard technique known in the art, depending on a host cell. Examples of the method include electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, a lithium acetate-DMSO technique, etc., but are not limited thereto.

Additionally, the term "operable linkage" means that the polynucleotide sequence is functionally linked to a promoter sequence that initiates and mediates transcription of the polynucleotide encoding the target protein of the present disclosure. The operable linkage can be prepared using a gene recombinant technique known in the art, and site-specific DNA cleavage and linkage can be prepared using a known lyase and ligase, but these are not limited thereto.

As used herein, the term "microorganism producing an aspartate-derived L-amino acid or amino acid derivative thereof" refers to a microorganism naturally producing an aspartate-derived L-amino acid or an amino acid derivative thereof, or refers to a microorganism in which the productivity of an aspartate-derived L-amino acid or amino acid derivative thereof is endowed to a parent strain lacking the ability to produce an aspartate-derived L-amino acid or an amino acid derivative thereof.

As used herein, the term "aspartate-derived L-amino acid or amino acid derivative thereof" refers to a material capable of being biosynthesized using aspartic acid (aspartate) as a precursor, and may interchangeably be used with the term "aspartate-derived product". The "amino acid derivative" refers to a material that can be produced from an L-amino acid and a material including a precursor of an L-amino acid. In addition, the amino acid derivative is not limited as long as it is a material that can be produced by biosynthesis using aspartate as a precursor. Specifically, materials synthesized by commonly using acetyl phosphate are included without limitation. For example, the amino acid derivative may be L-lysine, L-threonine, L-methionine, L-glycine, homoserine, O-acetylhomoserine, O-succinylhomoserine, O-phosphohomoserine, L-isoleucine, and cadaverine, but is not limited thereto.

Cadaverine may be directly biosynthesized using aspartate as a precursor, or may be produced from lysine by lysine decarboxylase. The L-methionine may be directly biosynthesized using aspartate as a precursor, or may be produced by converting from O-acetylhomoserine or O-succinylhomoserine.

As used herein, the term "aspartate (aspartic acid)" is abbreviated as Asp or D, and refers to aspartic acid, which is an α-amino acid used for biosynthesis of proteins. Like all other amino acids, aspartate includes an amino group and a carboxylic acid group. Generally, aspartate is produced as aspartyl phosphate by aspartokinase (LysC), and then converted into L-lysine, L-methionine, L-homoserine, L-threonine, L-isoleucine, etc. in the cell.

In order to enhance the biosynthesis of the aspartate-derived product, the aspartokinase variant of the present disclosure may be used. For example, in order to enhance the biosynthesis of L-lysine, L-threonine, L-methionine, L-glycine, homoserine, O-acetylhomoserine, O-succinylhomoserine, O-phosphohomoserine, L-isoleucine, and cadaverine, the aspartokinase variant of the present disclosure may be introduced or the activity thereof may be enhanced. In addition, the productivity of the aspartate-derived product can be further enhanced by introducing or enhancing the activity of a specific protein or by inactivating the activity of a specific protein.

The method of introducing, enhancing, and inactivating the activity of a specific protein may be carried out using a suitable method known in the art, depending on the characteristics of microorganisms.

The microorganism producing the aspartate-derived product, L-amino acid, or amino acid derivative thereof may be any microorganism capable of producing the aspartate-derived "amino acid" or amino acid derivative thereof by including the aspartate variant of the present disclosure. A specific example thereof may include *Escherichia* sp., *Serratia* sp., *Erwinia* sp., *Enterobacteria* sp., *Salmonella* sp., *Streptomyces* sp., *Pseudomonas* sp., *Brevibacterium* sp., or *Corynebacterium* sp., and more specifically, the microorganism may be *Corynebacterium glutamicum*, but is not limited thereto.

Still another aspect of the present disclosure provides a method for producing an aspartate-derived L-amino acid or an amino acid derivative thereof, comprising: culturing the above-described microorganism; and recovering the aspartate-derived L-amino acid or amino acid derivative thereof from the cultured microorganism or cultured medium.

The method for producing the aspartate-derived L-amino acid or amino acid derivative thereof may be easily determined by one of ordinary skill in the art under optimized culture conditions and enzyme activity conditions known in the art. Specifically, although not particularly limited to, the step of culturing the microorganism may be performed by batch culture, continuous culture, and fed-batch culture known in the art. Herein, the culture conditions are not particularly limited, but an optimal pH (e.g., pH 5 to 9, specifically pH 6 to 8, and most specifically pH 6.8) may be maintained by using a basic chemical (e.g., sodium hydroxide, potassium hydroxide, or ammonia) or an acidic chemical (e.g., phosphoric acid or sulfuric acid). In addition, an aerobic condition may be maintained by adding oxygen or an oxygen-containing gas mixture to a cell culture. The culture temperature may be maintained at 20° C. to 45° C., and specifically at 25° C. to 40° C., and the cultivation may be performed for about 10 hours to 160 hours, but these are not limited thereto. The aspartate-derived amino acid or amino acid derivative thereof produced by the culture may be secreted into a medium or may remain in cells.

Additionally, a medium to be used for culture may include sugar and carbohydrate (e.g., glucose, sucrose, lactose, fructose, maltose, molasses, starch, and cellulose), oil and fat (e.g., soybean oil, sunflower seed oil, peanut oil, and coconut oil), fatty acid (e.g., palmitic acid, stearic acid, and linoleic acid), alcohol (e.g., glycerol and ethanol), and organic acid (e.g., acetic acid) individually or in combination as a carbon source; a nitrogen-containing organic compound (e.g., peptone, yeast extract, meat juice, malt extract, corn solution, soybean meal powder, and urea) or an inorganic compound (e.g., ammonium sulfate, ammonium chloride, ammonium phosphate, ammonium carbonate, and ammonium nitrate) individually or in combination as a nitrogen source; and potassium dihydrogen phosphate, dipotassium phosphate, or a sodium-containing salt corresponding thereto individually or in combination as a phosphorous source; but these are not limited thereto. In addition, the medium may contain essential growth-promoting materials such as other metal salts (e.g., magnesium sulfate or iron sulfate), amino acids, and vitamins.

The method for recovering the aspartate-derived amino acid or amino acid derivative thereof produced in the culture method of the present disclosure may be carried out to collect a target amino acid from the cultured medium by using a suitable method known in the art according to the culture method. For example, centrifugation, filtration, anion-exchange chromatography, crystallization, and HPLC may be used, and the target aspartate-derived amino acid or amino acid derivative thereof may be recovered from the medium or microorganism by using a suitable method known in the art.

Additionally, the recovering method may further include a purification step, and may be carried out using a suitable method known in the art.

Still another aspect of the present disclosure provides a method for producing L-methionine, comprising: culturing the microorganism of the present disclosure; producing O-acetylhomoserine or O-succinylhomoserine from the cultured microorganism or cultured medium; and converting O-acetylhomoserine or O-succinylhomoserine to L-methionine.

Specifically, the "step of converting to L-methionine" may include a step of reacting O-acetylhomoserine or O-succinylhomoserine with O-acetylhomoserine sulfhydrylase or O-succinylhomoserine sulfhydrylase in the presence of a sulfide. The "O-acetylhomoserine or O-succinylhomoserine" may be a fermentation broth containing O-acetylhomoserine or O-succinylhomoserine produced by the microorganism of the present disclosure, or may be in a purified form. In addition, the "sulfide" may be, for example, methylmercaptan, and the methylmercaptan may refer to the form of sodium methyl mercaptan ($CH_3S$—Na) as well as methylmercaptan ($CH_3SH$) in a gas or liquefied state and methylmercaptan containing dimethylsulfide (DMS) in the form described in International Patent Publication No. WO2010/098629; and methylmercaptan may also refer to a methylmercaptan derivative containing a form capable of providing sulfur atoms. In addition, the "O-acetylhomoserine sulfhydrylase or O-succinylhomoserine sulfhydrylase" may be a fermentation broth of the microorganism producing the same, or may be a purified form.

The method for producing L-methionine may be easily determined by one of ordinary skill in the art under optimized culture conditions and enzyme activity conditions known in the art. The specific culture method and medium are as described above.

Advantageous Effects

The microorganism containing the aspartokinase variant according to the present disclosure may obtain the aspartate-derived L-amino acid or the aspartate-derived product in high yield without inhibiting the growth of host cells, as compared with a microorganism including the wild-type LysC.

BRIEF DESCRIPTION OF DRAWINGS

FIG. 1 shows a pathway for the biosynthesis of the aspartate-derived amino acid and amino acid derivative thereof of *Corynebacterium glutamicum*.

DETAILED DESCRIPTION OF THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation of lysC Variant-Introducing Strain

A variation, the activity of which can be enhanced compared to the wild-type, was selected through the structural modeling of a aspartokinase, and a strain introduced with the variant was prepared as described below.

In the gene lysC (SEQ ID NO: 2) encoding aspartokinase (SEQ ID NO: 1) derived from *Corynebacterium glutamicum* ATCC13032 (hereinafter referred to as WT), the amino acid at position 377 was selected as the variation site, and L-lysine, which is a basic amino acid, and L-methionine, which is a non-polar amino acid, were selected as representative examples of other amino acids for substitution.

In order to prepare a vector introduced with the variation, centering on the variation site, a pair of primers (SEQ ID NOS: 7 and 8 or SEQ ID NOS: 7 and 10) for amplifying the 5' upstream region and a pair of primers (SEQ ID NOS: 9 and 12 or SEQ ID NOS: 11 and 12) for amplifying the 3' downstream region were devised (Table 1). In the primers of SEQ ID NOS: 7 and 12, an XbaI restriction enzyme site (underlined) was inserted at each end. Further, in a pair of the primers of SEQ ID NOS: 8 and 9 or a pair of the primers of SEQ ID NOS: 10 and 11, a nucleotide substitution variation (underlined) was placed at the site designed to crossover with each other.

TABLE 1

| SEQ ID NO: | Primer | Sequence (5'-3') |
| --- | --- | --- |
| 7 | Primer 1 | TCC<u>TCTAGA</u>GCTGCGCAGTGTTGAATACG |
| 8 | Primer 2 | TGGAAATC<u>T</u>TTTCGATGTTCACGTTGACAT |
| 9 | Primer 3 | ACATCGAA<u>AA</u>GATTTCCACCTCTGAGATTC |
| 10 | Primer 4 | TGGAAATC<u>A</u>TTTCGATGTTCACGTTGACAT |
| 11 | Primer 5 | ACATCGAA<u>AT</u>GATTTCCACCTCTGAGATTC |
| 12 | Primer 6 | GAC<u>TCTAGA</u>GTTCACCTCAGAGACGATTA |

PCR was carried out with the primers of SEQ ID NOS: 7 and 8, SEQ ID NOS: 7 and 10, SEQ ID NOS: 9 and 12, or SEQ ID NOS: 11 and 12 using the chromosome of WT as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 30 seconds. Thereafter, the polymerization reaction was carried out at 72° C. for 7 minutes. As a result, centering on the variation site of the gene lysC, a DNA fragment (509 bp) of the 5' upstream region and a DNA fragment (520 bp) of the 3' downstream region were obtained, respectively.

PCR was carried out with the primers of SEQ ID NOS: 7 and 12 using the two amplified DNA fragments as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 60 seconds. Thereafter, the polymerization reaction was carried out at 72° C. for 7 minutes. As a result, a DNA fragment (1011 bp) including the variat (SEQ ID NO: 4) of the gene lysC encoding the aspartokinase variat (SEQ ID NO: 3), in which the leucine at position 377 is substituted with lysine, was amplified. In addition, in order to confirm the importance of the amino acid at position 377, a DNA fragment (1011 bp) including the variation (SEQ ID NO: 6) of the gene lysC encoding the aspartokinase variant (SEQ ID NO: 5), in which the leucine at position 377 is substituted with methionine, was obtained.

The vector pDZ (Korean Patent No. 0924065), which cannot be replicated in *Corynebacterium glutamicum*, and the DNA fragment (1011 bp) were treated with a restriction enzyme, XbaI, and these were linked using a DNA ligase and then cloned to obtain plasmids. The plasmids were named as pDZ-lysC(L377K) and pDZ-lysC(L377M).

The vectors, pDZ-lysC(L377K) and pDZ-lysC(L377M), were each transformed into WT using an electric pulse method (*Appl. Microbiol. Biotechnol.* (1999) 52:541-545), and then transformant strains were obtained in an LB medium containing kanamycin (25 mg/L). WT::lysC (L377K) and WT::lysC(L377M), the strains in which the nucleotide variation is introduced into the gene lysC by the DNA fragments inserted on the chromosome via a secondary recombinant process (crossover), were obtained, and these were named as *Corynebacterium glutamicum* CA01-2307 and CA01-2308, respectively. CA01-2307 and CA01-2308 were deposited to the Korea Culture Center of Microorganisms, which is an international depositary authority under the Budapest Treaty, on Mar. 29, 2017, and assigned Accessions Nos. KCCM12000P and KCCM12001P.

Example 2: Confirmation of Ability of lysC Variat Introducing Strain for Producing Aspartate-Derived Amino Acid In order to compare the abilities of the strains CA01-2307 and CA01-2308 obtained from Example 1 and the strain WT for producing major aspartate-derived amino acids, the strains were cultured using the following method, and the components in the culture medium were analyzed.

Each strain was inoculated into a corner-baffle flask (250 mL) containing a seed medium (25 mL), and cultured at 37° C. for 20 hours while shaking at 200 rpm. The seed culture solution (1 mL) was inoculated into a corner-baffle flask (250 mL) containing a production medium (24 mL), and then cultured at 37° C. for 24 hours while shaking at 200 rpm. The concentrations of L-lysine and L-threonine, which are representative amino acids derived from L-aspartate and aspartate, were analyzed by HPLC, and the analyzed concentrations are shown in Table 2.

<Seed Medium (pH 7.0)>

Glucose (20 g), peptone (10 g), yeast extract (5 g), urea (1.5 g), $KH_2PO_4$ (4 g), $K_2HPO_4$ (8 g), $MgSO_4.7H_2O$ (0.5 g), biotin (100 μg), thiamine HCl (1000 μg), calcium pantothenate (2000 μg), nicotinamide (2000 μg) (in 1 L of distilled water)

<Production Medium (pH 7.0)>

Glucose (100 g), $(NH_4)_2SO_4$ (40 g), soy protein (2.5 g), corn steep solids (5 g), urea (3 g), $KH_2PO_4$ (1 g), $MgSO_4.7H_2O$ (0.5 g), biotin (100 μg), thiamine chloride (1000 μg), calcium pantothenate (2000 μg), nicotinamide (3000 μg), $CaCO_3$ (30 g) (in 1 L of distilled water)

TABLE 2

Concentrations of aspartate-derived amino acids produced from CA01-2307 and CA01-2308

| Strain | Concentration | | |
|---|---|---|---|
| | L-Aspartate (mg/L) | L-Lysine (mg/L) | L-Threonine (mg/L) |
| WT | 20.3 | 8.0 | 340.3 |
| CA01-2307 | 29.7 | 3647.7 | 402.7 |
| CA01-2308 | 30.2 | 1572.3 | 385.4 |

As a result of analyzing the concentrations of the aspartate-derived amino acids, it was confirmed that when the lysC variation was introduced, the concentration of L-lysine was dramatically increased and those of L-aspartate and L-threonine were also increased compared to WT. Based on the results above, the strains CA01-2307, CA01-2308, and WT were cultured in the same manner as described above in order to compare the abilities thereof for producing lysine in detail. Further, the concentration of L-lysine in the culture medium was analyzed in the same manner as described above (Table 3).

TABLE 3

Concentrations of L-lysine produced from strains WT, CA01-2307, and CA01-2308

| Strain | L-Lysine (g/L) Concentration | | |
|---|---|---|---|
| | Batch 1 | Batch 2 | Batch 3 |
| WT | 0.008 | 0.007 | 0.008 |
| CA01-2307 | 3.664 | 3.665 | 3.598 |
| CA01-2308 | 1.523 | 1.475 | 1.666 |

As a result of analyzing the concentration of L-lysine, it was confirmed that the productivity of L-lysine produced from CA01-2307 including the lysC(L377K) variation was greatly increased as in the previous evaluation compared to that produced from the strain WT. In addition, it was confirmed that the productivity of L-lysine produced from CA01-2308 including the lysC(L377M) variation also increased compared to that produced from the strain WT. Based on the results above, it was confirmed that the productivity of L-lysine in the aspartate-derived amino acids was greatly increased due to the aspartokinase variant (SEQ ID NO: 3), in which the leucine at position 377, which is selected in the present disclosure, is substituted with lysine, and due to the aspartokinase variant (SEQ ID NO: 5), in which the leucine at position 377 is substituted with methionine.

Example 3: Preparation of L-Threonine-Enhanced Strain and Confirmation of Productivity of L-Threonine In order to clearly confirm the change in the L-threonine productivity by the introduction of the lysC(L377K) variation, which has the higher lysine productivity confirmed in Example 2, a variation was introduced into the gene encoding homoserine dehydrogenase producing homoserine, which is a common intermediate in the biosynthetic pathway of L-threonine, L-isoleucine, L-methionine, and homoserine derivatives. Specifically, a strain was prepared by introducing the hom(G378E) variation known in the art (*Appl. Microbiol. Biotechnol.* 45, 612-620 (1996)) into the strain CA01-2307, which was prepared in Example 1. In addition, a strain in which the hom(G378E) variation is introduced into WT was also prepared as a control group. In order to prepare a vector introducing the hom(G378E), PCR was carried out with SEQ ID NOS: 13 and 14 and SEQ ID NOS: 15 and 16 using WT genomic DNA as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 30 seconds. Thereafter, the polymerization reaction was carried out at 72° C. for 7 minutes.

As a result, centering on the variation of the gene hom, a DNA fragment (220 bp) of the 5' upstream region and a DNA fragment (220 bp) of the 3' downstream region were obtained. PCR was carried out with SEQ ID NOS: 13 and 16 using these two PCR products as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 30 seconds. Thereafter, the polymerization reaction was carried out at 72° C. for 7 minutes. As a result, a DNA fragment (440 bp) including the variation of the gene hom was amplified.

TABLE 4

| SEQ ID NO: | Primer | Sequence (5'-3') |
|---|---|---|
| 13 | Primer 7 | TCC<u>TCTAGA</u>CTGGTCGCCTGATGTTCTAC |
| 14 | Primer 8 | GCCAAAACCTCCACGCGATC |

TABLE 4-continued

| SEQ ID NO: | Primer | Sequence (5'-3') |
|---|---|---|
| 15 | Primer 9 | ATCGCGTGGAGGTTTTGGCT |
| 16 | Primer 10 | GACTCTAGATTAGTCCCTTTCGAGGCGGA |

The vector pDZ, which was previously used in Example 1, and DNA fragment (440 bp) were treated with a restriction enzyme, XbaI, and these were linked using a DNA ligase and then cloned to obtain a plasmid. The plasmid was named as pDZ-hom(G378E).

The vector, pDZ-hom(G378E), was introduced into the strains WT and CA01-2307 using an electric pulse method (Appl. Microbiol. Biotechnol. (1999, 52:541-545)), and then transformant strains were obtained in a selective medium containing kanamycin (25 mg/L). WT::hom(G378E) and CA01-2307::hom(G378E), the strains in which the nucleotide variation was introduced into the gene hom by the DNA fragment inserted on the chromosome via a secondary recombinant process (crossover), were obtained. In order to compare abilities of WT::hom(G378E) and CA01-2307::hom(G378E) for producing threonine, the strains were cultured in the same manner as in Example 2, and the concentration of threonine in the culture medium was analyzed.

TABLE 5

Concentrations of threonine produced from strains, WT::hom(G378E) and CA01-2307::hom(G378E)

| Strain | L-Threonine (g/L) Concentration | | |
|---|---|---|---|
| | Batch 1 | Batch 2 | Batch 3 |
| WT::hom(G378E) | 0.456 | 0.475 | 0.432 |
| CA01-2307::hom(G378E) | 1.210 | 1.132 | 1.211 |

As a result of analyzing the concentration of L-threonine, it was confirmed that the productivity of L-threonine was dramatically increased in the strain including the lysC variation (Table 5).

Example 4: Preparation of L-Isoleucine-Enhanced Strain and Comparison of Productivity of L-Isoleucine In order to confirm the effect of the introduction of the lysC(L377K) variation on the L-isoleucine productivity, a vector for enhancing expression of the ilvA(V323A) variation of the gene (Appl. Enviro. Microbiol., December 1996, p. 4345-4351) encoding L-threonine dehydratase, which is known in the art, was prepared.

In order to prepare a vector introduced with the variation of the gene ilvA, centering on the variation site, a pair of primers (SEQ ID NOS: 17 and 18) for amplifying the 5' upstream region and a pair of primers (SEQ ID NOS: 19 and 20) for amplifying the 3' downstream region were devised. In the primers of SEQ ID NOS: 17 and 20, a BamHI restriction enzyme site (underlined) was inserted at each end. Further, in the primers of SEQ ID NOS: 18 and 19, a nucleotide substitution variation (underlined) was placed at the site designed to crossover with each other.

TABLE 6

| SEQ ID NO: | Primer | Sequence (5'-3') |
|---|---|---|
| 17 | Primer 11 | ACGGATCCCAGACTCCAAAGCAAA AGCG |
| 18 | Primer 12 | ACACCACGGCAGAACCAGGTGCAA AGGACA |
| 19 | Primer 13 | CTGGTTCTGCCGTGGTGTGCATCAT CTCTG |
| 20 | Primer 14 | ACGGATCCAACCAAACTTGCTCACA CTC |

PCR was carried out with the primers of SEQ ID NOS: 17 and 18 and SEQ ID NOS: 19 and 20 using the chromosome of WT as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 30 seconds. Thereafter, the polymerization reaction was carried out at 72° C. for 7 minutes. As a result, centering on the variation site of the gene ilvA, a DNA fragment (627 bp) of the 5' upstream region and a DNA fragment (608 bp) of the 3' downstream region were obtained.

PCR was carried out with the primers of SEQ ID NOS: 17 and 20 using the two amplified DNA fragments as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 60 seconds. Thereafter, the polymerization reaction was carried out at 72° C. for 7 minutes. As a result, a DNA fragment (1217 bp) including the variation of the gene ilvA encoding the IlvA variant, in which the valine at position 323 is substituted with alanine, was amplified.

The vector pECCG117 (Korean Patent No. 10-0057684) and DNA fragment (1011 bp) were treated with a restriction enzyme, BamHI, and these were linked using a DNA ligase and then cloned to obtain a plasmid. The plasmid was named as pECCG117-ilvA(V323A).

The vector pECCG117-ilvA(V323A) was introduced into the strains WT::hom(G378E) and CA01-2307::hom(G378E), which were prepared in Example 3, using an electric pulse method, and then smeared on a selective medium containing kanamycin (25 mg/L) to obtain the transformant strains.

The strains were cultured in the same manner as in the flask culture method shown in Example 2, and the concentration of L-isoleucine in the culture medium was analyzed (Table 7).

TABLE 7

| Strain | L-Isoleucine (g/L) | | |
|---|---|---|---|
| | Batch 1 | Batch 2 | Batch 3 |
| WT::hom(G378E)/pECCG117-ilvA(V323A) | 0.102 | 0.072 | 0.062 |
| CA01-2307::hom(G378E)/ pECCG117-ilvA(V323A) | 0.876 | 0.900 | 0.918 |

As a result of analyzing the concentration of L-isoleucine, it was confirmed that the productivity of L-isoleucine was greatly increased in the strain including the lysC variation.

Example 5: Preparation of O-Acetylhomoserine-Enhanced Strain and Comparison of Productivity of O-Acetylhomoserine In order to determine the effect of introduction of the lysC(L377K) variation on the production of O-acetylhomoserine, the gene metB, which encodes the cystathionine gamma-synthase involved in the O-acetylhomoserine degradation pathway, and the gene metY, which encodes O-acetylhomoserine (thiol)-lyase, were deleted, and then the gene metX encoding the homoserine O-acetyltransferase, which is an O-acetylhomoserine biosynthetic enzyme, was overexpressed, and thereby the strain producing O-acetylhomoserine was prepared. First, in order to delete the gene metB, based on the nucleotide sequence information of the gene, metB derived from WT, a pair of primers (SEQ ID NOS: 21 and 22) for amplifying the 5' upstream region of the gene metB and a pair of primers (SEQ ID NOS: 23 and 24) for amplifying the 3' downstream region were devised.

TABLE 8

| SEQ ID NO: | Primer | Sequence (5'-3') |
| --- | --- | --- |
| 21 | Primer 15 | TCTAGATGCGCTGATTATCTCACC |
| 22 | Primer 16 | ACTGGTGGGTCATGGTTGCATATG AGATCAACTCCTGTAA |
| 23 | Primer 17 | TTACAGGAGTTGATCTCATATGCA ACCATGACCCACCAGT |
| 24 | Primer 18 | TCTAGACCTTGAAGTTCTTGACTG |

PCR was carried out with the primers of SEQ ID NOS: 21 and 22, SEQ ID NO: 23 and 24 using the chromosome of WT as a template. After denaturation at 95° C. for 5 minutes, PCR was carried out for a total of 30 cycles under the following conditions: 95° C. denaturation for 30 seconds, annealing at 55° C. for 30 seconds, polymerization at 72° C. for 90 seconds. Thereafter, the polymerization reaction was carried out at 72° C. for 7 minutes. As a result, a DNA fragment (450 bp) of the 5' upstream region of the gene metB and a DNA fragment (467 bp) of the 3' downstream region were obtained.

PCR was carried out with the primers of SEQ ID NOS: 21 and 24 using the two amplified DNA fragments as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 3 minutes. Thereafter, the polymerization reaction was carried out at 72° C. for 7 minutes. As a result, the central region of the gene metB was deleted, and thus a DNA fragment (917 bp) including only the upstream and downstream ends was amplified.

The vector pDZ and DNA fragment (917 bp) were treated with a restriction enzyme, XbaI, and these were linked using a DNA ligase and then cloned to obtain a plasmid. The plasmid was named as pDZ-ΔmetB.

The vector pDZ-ΔmetB was introduced into the strains WT::hom(G378E) and CA01-2307::hom(G378E), which were prepared in Example 3, using an electric pulse method, and then the transformant strains were obtained from a selective medium containing kanamycin (25 mg/L). WT:: hom(G378E)ΔmetB and CA01-2307::hom(G378E)ΔmetB, the strains in which the metB gene is deleted by the DNA fragments inserted on the chromosome via a secondary recombinant process (crossover), were obtained.

In order to delete the gene metY involved in another degradation pathway of O-acetylhomoserine, based on the nucleotide sequence information of the gene, metY derived from WT, a pair of primers (SEQ ID NOS: 25 and 26) for amplifying the 5' upstream region of the gene metY and a pair of primers (SEQ ID NOS: 27 and 28) for amplifying the 3' downstream region were devised.

TABLE 9

| SEQ ID NO: | Primer | Sequence (5'-3') |
| --- | --- | --- |
| 25 | Primer 19 | TCTAGAAGTAGCGTTGCTGTACAC |
| 26 | Primer 20 | ATCAATGGTCTCGATGCCCATATG GCATTTGGAGGTCCTTAAG |
| 27 | Primer 21 | CTTAAGGACCTCCAAATGCCATAT GGGCATCGAGACCATTGAT |
| 28 | Primer 22 | TCTAGATGGAACCGTTGCAACCAC |

PCR was carried out with SEQ ID NOS: 25 and 26, SEQ ID NO: 27 and 28 using the chromosome of WT as a template. After denaturation at 95° C. for 5 minutes, PCR was carried out for a total of 30 cycles under the following conditions: 95° C. denaturation for 30 seconds, annealing at 55° C. for 30 seconds, polymerization at 72° C. for 90 seconds. Thereafter, the polymerization reaction was carried out at 72° C. for 7 minutes. As a result, a DNA fragment (512 bp) of the 5' upstream region of the gene metY and a DNA fragment (520 bp) of the 3' downstream region were obtained.

PCR was carried out with the primers of SEQ ID NOS: 25 and 28 using the two amplified DNA fragments as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 3 minutes. Thereafter, the polymerization reaction was carried out at 72° C. for 7 minutes. As a result, the central region of the gene metY was deleted, and thus a DNA fragment (1032 bp) including only the upstream and downstream ends was amplified.

The vector pDZ and DNA fragment (1032 bp) were treated with a restriction enzyme, XbaI, and these were linked using a DNA ligase and then cloned to obtain a plasmid. The plasmid was named as pDZ-ΔmetY.

The vector pDZ-ΔmetY was introduced into each of the strains WT::hom(G378E)ΔmetB and CA01-2307::hom (G378E)ΔmetB, which were prepared in the above, using an electric pulse method, and then the transformant strains were obtained in a selective medium containing kanamycin (25 mg/L). WT::hom(G378E)ΔmetBΔmetY and CA01-2307:: hom(G378E)ΔmetBΔmetY, the strains in which the gene metY was deleted by the DNA fragments inserted on the chromosome via a secondary recombinant process (crossover), were obtained.

In order to maximize the production of O-acetylhomoserine, a vector for enhancing the expression of the gene metX was prepared. To amplify the gene encoding homoserine O-acetyltransferase (MetX), based on the reported WT-derived sequences, the vector was devised by inserting a BamHI restriction enzyme region at both ends of the primers (SEQ ID NOS: 29 and 30) for amplifying from the promoter region (about 300 bp upstream of the initiation codon) to the terminator region (about 100 bp downstream of the termination codon).

TABLE 10

| SEQ ID NO: | Primer | Sequence (5'-3') |
|---|---|---|
| 29 | Primer 23 | GGATCCCCTCGTTGTTCACCCAGC AACC |
| 30 | Primer 24 | GGATCCCAAAGTCACAACTACTTA TGTTAG |

PCR was conducted with the primers of SEQ ID NOS: 25 and 26 using the chromosome of WT as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 90 seconds. Thereafter, the polymerization reaction was carried out at 72° C. for 7 minutes. As a result, a DNA fragment (1546 bp) including the gene metX was obtained.

The vector pECCG117 (Korean Patent No. 10-0057684) and DNA fragment of metX were treated with a restriction enzyme, BamHI, and these were linked using a DNA ligase and then cloned to obtain a plasmid. The plasmid was named as pECCG117-metX.

The vector pECCG117-metX was introduced into the strains WT::hom(G378E)ΔmetBΔmetY and CA01-2307::hom(G378E)ΔmetBΔmetY, which were prepared in the above, using an electric pulse method, and then smeared on a selective medium containing kanamycin (25 mg/L) to obtain the transformant strains.

In order to compare the abilities of the strains prepared above for producing O-acetylhomoserine (hereinafter referred to as O-AH), the strains were cultured using the method below and the concentration of O-acetylhomoserine in the culture medium was analyzed.

One platinum loop of the strains was inoculated into a corner-baffle flask (250 mL) containing an O-AH production medium (25 mL), and cultured at 37° C. for 20 hours while shaking at 200 rpm. The concentration of O-acetylhomoserine was analyzed by HPLC, and the analyzed concentration is shown in Table 11.

<O-AH Production Medium (pH 7.0)>

Glucose (100 g), $(NH_4)_2SO_4$ (40 g), soy protein (2.5 g), corn steep solids (5 g), urea (3 g), $KH_2PO_4$ (1 g), $MgSO_4 \cdot 7H_2O$ (0.5 g), biotin (100 μg), thiamine chloride (1000 μg), calcium pantothenate (2000 μg), nicotinamide (3000 μg), $CaCO_3$ (30 g), L-methionine (0.3 g) (in 1 L of distilled water).

TABLE 11

| | O-Acetylhomoserine (g/L) | | |
|---|---|---|---|
| Strain | Batch 1 | Batch 2 | Batch 3 |
| WT::hom(G378E)ΔmetBΔmetY/ pECCG117-metX | 0.135 | 0.209 | 0.175 |
| CA01-2307::hom(G378E)ΔmetBΔmetY/ pECCG117-metX | 2.312 | 2.045 | 2.532 |

As a result of analyzing the concentration of O-acetylhomoserine as shown in the table above, it was confirmed that the concentration of O-acetylhomoserine produced by the lysC variation was increased.

Example 6: Preparation of O-Succinylhomoserine-Enhanced Strain and Comparison of Productivity of O-Succinylhomoserine In order to determine the influence of the introduction of the lysC(L377K) variation on the production of O-succinylhomoserine, the strain producing O-succinylhomoserine was prepared. Since wild-type *Corynebacterium glutamicum* does not naturally produce O-succinylhomoserine, the strain was modified to have the activity of O-succinyltransferase (MetX) by the substitution of the amino acid at the substrate binding region of the O-acetyltransferase, which was prepared in Example 5, in order to produce O-succinylhomoserine. Accordingly, based on the sequences of the gene, WT-derived metX, a pair of primers (SEQ ID NOS: 31 and 32) was devised to prepare the vector for introducing the metX variation.

TABLE 12

| SEQ ID NO: | Primer | Sequence (5'-3') |
|---|---|---|
| 31 | Primer 25 | TCTAGAATGCCCACCCTCGCGCCTTC |
| 32 | Primer 26 | TCTAGATTAGATGTAGAACTCGATG |

PCR was carried out with the primers of SEQ ID NOS: 27 and 28 using the chromosome of WT as a template. After denaturation at 95° C. for 5 minutes, PCR was carried out for a total of 30 cycles under the following conditions: 95° C. denaturation for 30 seconds, annealing at 55° C. for 30 seconds, and polymerization at 72° C. for 90 seconds. Thereafter, the polymerization reaction was carried out at 72° C. for 7 minutes. As a result, a DNA fragment (1146 bp) of the encoding region of the gene metX was obtained.

The vector pDZ and DNA fragment (1146 bp) were treated with a restriction enzyme, XbaI, and these were linked using a DNA ligase and then cloned to obtain a plasmid. The plasmid was named as pDZ-metX. Based on the vector pDZ-metX, in order to make a variation vector, in which the amino acid at position 176 is substituted with asparagine and the amino acid at position 313 is substituted with arginine, a pair of primers (SEQ ID NOS: 33 and 34), which cause a variation on the amino acid at position 176, and a pair of primers (SEQ ID NOS: 35 and 36), which cause a variation on the amino acid at position 313, were devised.

TABLE 13

| SEQ ID NO: | Primer | Sequence (5'-3') |
|---|---|---|
| 33 | Primer 27 | ACGCGCCAGCGCCTGGAACATCGGCA TTCAATCCG |
| 34 | Primer 28 | CGGATTGAATGCCGATGTTCCAGGCG CTGGCGCGT |
| 35 | Primer 29 | TAGATACCGATATTCGGTACCCCTAC CACCAG |

TABLE 13-continued

| SEQ ID NO: | Primer | Sequence (5'-3') |
|---|---|---|
| 36 | Primer 30 | CTGGTGGTAGGGGTACCGAATATCGG TATCTAC |

The variant gene metX was prepared using a site-directed mutagenesis kit (Stratagene, USA) together with each of the primers above. The transformant plasmid based on the existing wild-type plasmid pDZ-metX was named as pDZ-metX(Q176N, L313R). The vector pDZ-metX(Q176N, L313R), which was prepared above, was transformed into the strains WT::hom(G378E)ΔmetBΔmetY and CA01-2307::hom(G378E)ΔmetBΔmetY prepared in Example 5 using an electric pulse method, and then the transformant strains were obtained in a selective medium containing kanamycin (25 m g/L). WT::hom(G378E)metX(Q176N, L313R)ΔmetBΔmetY and CA01-2307::hom(G378E)metX (Q176N, L313R)ΔmetBΔmetY, the strains in which the gene metX is replaced with metX(Q176N, L313R) by the DNA fragment inserted on the chromosome via a secondary recombinant process (crossover), were obtained.

In order to maximize the production of O-succinylhomoserine, a vector for enhancing the expression of the variant gene metX(Q176N, L313R) was prepared. Based on pECCG117-metX prepared in Example 5, a vector overexpressing the variant metX was prepared using primers of SEQ ID NOS: 33 to 36, in which the variant amino acid at position at position 176, which has the activity of O-succinyltransferase, is substituted with asparagine and the amino acid at position 313 is substituted with arginine. Specifically, the vector was prepared using a site-directed mutagenesis kit (Stratagene, USA) together with each of the primers, and the prepared vector was named as pECCG117-metX(Q176N, L313R).

pECCG117-metX(Q176N, L313R) and the empty vector pECCG117 were introduced into WT::hom(G378E)metX (Q176N, L313R)ΔmetBΔmetY and CA01-2307::hom (G378E)metX(Q176N, L313R)ΔmetBΔmetY, which are the above-prepared strains producing O-succinylhomoserine, using an electric pulse method, and smeared on a selective medium containing kanamycin (25 mg/L) to obtain the transformant strain.

In order to compare the ability of the strain for producing O-succinylhomoserine, the strain was cultured using the following methods, and the concentration of O-succinylhomoserine in the culture medium was analyzed.

One platinum loop of the strain was inoculated into a corner-baffle flask (250 mL) containing 25 mL of the same O-AH production medium composition used in Example 5, and cultured at 37° C. for 20 hours while shaking at 200 rpm. The concentration of O-succinylhomoserine was analyzed by HPLC, and the analyzed concentration is shown in Table 14.

TABLE 14

| Strain | O-Succinylhomoserine (g/L) | | |
|---|---|---|---|
| | Batch 1 | Batch 2 | Batch 3 |
| WT::hom(G378E)metX(Q176N, L313R)ΔmethBΔmetY/ pECCG117-metX(Q176N, L313R) | 0.052 | 0.120 | 0.087 |
| CA01-2307::hom(G378E)ΔmetBΔmetY/ pECCG117-metX(Q176N, L313R) | 1.529 | 1.632 | 1.874 |

As a result of analyzing the concentration of O-succinylhomoserine as shown in the table above, it was confirmed that the production of O-succinylhomoserine produced by the lysC variation was increased.

These results suggest that the variant of the present disclosure can increase the production of the aspartate-derived amino acid and/or derivative thereof.

From the foregoing, one of ordinary skill in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

What is claimed is:

1. An aspartokinase variant having at least 80% sequence identity to SEQ ID NO: 1 having aspartokinase activity, wherein the amino acid at position 377 in the amino acid sequence of SEQ ID NO: 1 is substituted with L-lysine or L-methionine.

2. A polynucleotide encoding the variant of claim 1.

3. A microorganism of the genus *Corynebacterium*, which produces an aspartate-derived L-amino acid or an amino acid derivative thereof comprising the aspartokinase variant of claim 1, wherein the aspartate-derived L-amino acid or amino acid derivative thereof is selected from the group consisting of lysine, threonine, methionine, homoserine, O-acetylhomoserine, O-succinylhomoserine, isoleucine, and cadaverine.

4. The microorganism according to claim 3, wherein the microorganism of the genus *Corynebacterium* is *Corynebacterium glutamicum*.

5. A method for producing an aspartate-derived L-amino acid or an amino acid derivative thereof, comprising:

culturing the microorganism of claim 3 in a medium; and recovering the aspartate-derived L-amino acid or amino acid derivative thereof from the cultured microorganism or cultured medium, wherein the aspartate-derived L-amino acid or amino acid derivative thereof is selected from the group consisting of lysine, threonine, methionine, homoserine, O-acetylhomoserine, O-succinylhomoserine, isoleucine, and cadaverine.

6. The method according to claim 5, wherein the microorganism of the genus *Corynebacterium* is *Corynebacterium glutamicum*.

7. A method for producing L-methionine, comprising:

culturing the microorganism of claim 3 in a medium;

producing O-acetylhomoserine or O-succinylhomoserine from the cultured microorganism or cultured medium; and converting the O-acetylhomoserine or O-succinylhomoserine to L-methionine.

8. The method according to claim 7, wherein the microorganism of the genus *Corynebacterium* is *Corynebacterium glutamicum*.

\* \* \* \* \*